(12) United States Patent
Waller et al.

(10) Patent No.: US 6,329,549 B1
(45) Date of Patent: Dec. 11, 2001

(54) DIMETHYL ETHER FOR METHYL GROUP ATTACHMENT ON A CARBON ADJACENT TO AN ELECTRON WITHDRAWING GROUP

(75) Inventors: Francis Joseph Waller, Allentown; Gene Everad Parris, Coopersburg, both of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/544,672

(22) Filed: Apr. 6, 2000

(51) Int. Cl.$^7$ .................................................. C07C 51/42
(52) U.S. Cl. .......................... 562/608; 560/265; 558/467; 558/303
(58) Field of Search ........................... 562/608; 560/265; 558/467, 303

(56) References Cited

U.S. PATENT DOCUMENTS

| | | |
|---|---|---|
| 4,442,307 | 4/1984 | Lewis et al. .................. 568/470 |
| 4,721,810 * | 1/1988 | Hargis . |
| 4,736,062 | 4/1988 | Hagen et al. .................. 562/599 |
| 4,761,393 | 8/1988 | Baleiko et al. ................. 502/170 |
| 4,801,571 | 1/1989 | Montag et al. ................. 502/236 |
| 4,845,070 | 7/1989 | Montag ........................ 502/243 |
| 4,942,258 | 7/1990 | Smith ........................... 562/599 |
| 5,710,328 | 1/1998 | Spivey et al. .................. 562/599 |
| 5,808,148 | 9/1998 | Gogate et al. ................. 562/599 |

OTHER PUBLICATIONS

Hathaway et al., "Base catalysis by alkali modified zeolites. III. Alkylation with methanol" in J. Catal. (1989), 119(2), 497–507.*

"Novel Catalysts for the Environmentally Friendly Synthesis of Methyl Methacrylate", JJ Spivey, Ind. Eng. Chem. 36, (1997) PP 4600–4608.

"Catalytic Synthesis of Methacrylates over Silica Supported Niobium Catalysts", Symposium, 217$^{th}$ National Meeting, Am. Chem. Soc., Mar. 21–25, 1999.

"FePO Catalysts for the Selective Oxidative Dehydrogenation of Isobutyric Acid Into Methacrylic Acid", Catal. Rev. Sci. Eng., 40, (1998) PP 1–38.

"Formation of Methacrylic Acid by Oxidative dehydrogenation of isobutyric acid; promoters of iron phosphate catalysts", M. Ai, Appl. Cata. A: Gen., 109, (1994) PP 135–146.

"Oxidative Dehydrogenation of Isobutyric Acid on V2O5–P2)5 Catalysts", Jour. Of Cata., 98, (1986) PP 401–410.

"Vapor–Phase Aldol Condensation of Formaldehyde with Propionic Acid on Vanadium Pentoxide–Phosphorus Pentoxide", Appl. Cata., 36,(1998) pp. 221–230.

"The Production of Methacrylic Acid by the Vapor–Phase Aldol Condensation of Propionic Acid With Formaldehyde", Jour. Cata., 124, (1990) PP 293–296.

"Vapor–Phase Aldol Condensation of Formaldehyde with Acetic Acid on V2O5–P2O5 Catalysts", Jour. Cata. 107, (1987) pp. 201–208.

"Oxydehydrogenation of Isobutyric Acid with Heteropolyacid Catalysts: Experimental Observations of Deactivation", Jour. Cata. 124, (1990) pp. 247–258.

"Selective Catalytic C–C Bond Formation on Magnesium Oxide to Produce a, B–Unsaturated Compounds", Kurokawa, Heter. Cata. And Fine Chem., (1988) pp. 299–306.

* cited by examiner

Primary Examiner—Ralph Gitomer
Assistant Examiner—D. Khare
(74) Attorney, Agent, or Firm—Robert J. Wolff

(57) ABSTRACT

A process for methylating an alpha carbon adjacent to an electron withdrawing group includes reacting dimethyl ether with a molecule containing the alpha carbon and the electron withdrawing group to substitute a methyl group on the alpha carbon. The process can be conducted in a vapor phase and can be represented by Equation I:

$$R(CH_2)_nCH_2\text{-}EWG+CH_3OCH_3 \rightarrow R(CH_2)_nCH(CH_3)\text{-}EWG+CH_3OH \quad (I)$$

where EWG is the electron withdrawing group, and R is H when n is 0, 1 or 2, and R is alkyl, EWG or aryl when n>2. For example, the molecule reacted with dimethyl ether can be acetic acid, propionic acid, methyl acetate, methyl propionate, acetonitrile, propionitrile and acetone. The process is catalyzed by an acid catalyst containing a Lewis acid functionality. When the electron withdrawing group is an acid, a methyl ester can be formed by esterifying the electron withdrawing group with methanol liberated from dimethyl ether. When the process is conducted in the presence of an oxidant, such as oxygen, an α,β-unsaturated bond can be formed in the molecule according to Equation II:

$$R(CH_2)_nCH(CH_3)\text{-}EWG+½O_2 \rightarrow R(CH_2)_nC(=CH_2)\text{-}EWG+H_2O \quad (II)$$

where EWG is the electron withdrawing group, and R is H when n is 0, 1 or 2, and R is alkyl, EWG or aryl when n>2.

24 Claims, No Drawings

DIMETHYL ETHER FOR METHYL GROUP ATTACHMENT ON A CARBON ADJACENT TO AN ELECTRON WITHDRAWING GROUP

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to the attachment of a methyl group on a carbon adjacent to an electron withdrawing group using dimethyl ether as the source of the methyl group. In another aspect it relates to the in situ conversion of the attached methyl group on a carbon adjacent to an electron withdrawing group to a double bond when oxygen or other oxidant is present with the dimethyl ether.

The attachment of a methyl group on a carbon adjacent to an electron withdrawing group or the formation of a carbon-carbon double bond is problematic at an industrial scale.

One approach is to form an enolate, that is, removing the proton on a carbon adjacent to an electron withdrawing group with a base to form a carbanion. When the electron withdrawing group contains a carbonyl group the combination of the carbanion and the carbonyl is an enolate. In organic chemistry alkylation of the enolate is done with a methyl halide such as methyl iodide.

Another approach reacts intermediates, such as propionic acid, propionic acid anhydride, or methyl propionate with formaldehyde or formaldehyde dimethylacetal or trioxane or paraformaldehyde to form methacrylic acid or methyl methacrylate. Although formaldehyde can be added in excess, the preferred modes of operation utilize the carboxylic acid intermediates in excess to avoid significant yield loss due to formaldehyde side reactions in the gas phase.

For example, in U.S. Pat. No. 4,736,062, Hagen et al. disclose a process of producing an alpha, beta-ethylenically unsaturated monocarboxylic acid compound which comprises the aldol-type condensation of a saturated aliphatic monocarboxylic acid and formaldehyde under vapor phase conditions in the presence of a hydrocarbon of 6 to 12 carbon atoms and a solid catalyst. This solid acid catalyst is described as comprising a cation of Group I or Group II metal and a silica support.

In U.S. Pat. No. 4,761,393, Baleiko et al. describe an in situ method for preparing an alkali metal ion-bearing particulate siliceous catalyst suitable for enhancing the vapor-phase condensation of a gaseous, saturated carboxylic acid with formaldehyde.

In U.S. Pat. No. 4,801,571 Montag et al. disclose a mixed oxide $SiO_2$—$SnO_2$—Cs ion catalyst and process for production of an alpha, beta-ethylenically unsaturated monocarboxylic acid by condensation of a saturated monocarboxylic acid with formaldehyde.

In U.S. Pat. No. 4,845,070, Montag describes a catalyst suitable for production of methacrylic acid by condensation of propionic acid with formaldehyde. The catalyst comprises a support which consists essentially of porous silica gel with cesium ions on the catalyst support surface, this support surface having a surface area of about 50 to about 150 $M^2/g$, a porosity of less than about 1 $cm^3/gm$, a pore size distribution such that less than about 10 percent of the pores present in the catalyst have a pore diameter greater than about 750 angstroms, and the cesium ions present in an amount of about 4 to about 10 percent by weight of the said catalyst.

In U.S. Pat. No. 4,942,258, Smith discloses a process for regeneration of a catalyst which comprises a support which consists essentially of porous silica with cesium ions on the catalyst support surface, said catalyst useful for production of methacrylic acid by condensation of propionic acid with formaldehyde.

In U.S. Pat. No. 5,710,328, Spivey et al. disclose a process for the preparation of alpha,beta-unsaturated carboxylic acids and the corresponding anhydrides which comprises contacting formaldehyde or a source of formaldehyde with a carboxylic anhydride in the presence of a catalyst comprising mixed oxides of vanadium and phosphorous, and optionally containing a third component selected from titanium, aluminum, or preferably silicon. In Ind. Eng. Chem. Res., Vol. 36, No.11, 1997, 4600–4608, Spivey et al. report that the highest yields of methacrylic acid were obtained with the Vanadium-Silicon-Phosphorous ternary oxide catalyst with V—Si—P atomic ratio of 1:10:2.8.

In U.S. Pat. No. 5,808,148, Gogate et al. disclose a process for the preparation of alpha,beta-unsaturated carboxylic acids and esters which comprises contacting formaldehyde or a source of formaldehyde with a carboxylic acid, ester, or a carboxylic acid anhydride in the presence of a catalyst comprising an oxide of niobium. The optimum catalyst in the catalytic synthesis of methacrylates comprised a mixed niobium oxide-silica composition containing 10% Nb2O5 (Ind. Eng. Chem. Res., Vol. 36, No.11, 1997, 4600–4608; Symposium Syngas Conversion to Fuels and Chemicals, Div. Pet. Chem., Inc., 217th National Meeting, American Chemical Society, Anaheim, Calif., 1999, 34–36).

In a related approach to synthesizing methyl methacrylate, the synthesis of isobutyric acid is followed by oxidative dehydrogenation to yield methacrylic acid, which is then esterified with methanol to yield methyl methacrylate. The key technical challenge lies in the selective oxidative dehydrogenation of isobutyric acid to methacrylic acid and three classes of catalysts have been disclosed: 1) iron phosphates, 2) vanadium-phosphorous mixed oxides or with a ternary component, and 3) heteropolyacids based on phosphomolybdic acid.

In Catalysis Reviews, Sci. Eng. 40(1&2), 1–38, (1998), Millet presents a comprehensive review of iron phosphate catalysts disclosed in the patent literature. According to Millet, the optimum catalysts for this process have P/Fe ratio greater than 1.0, are promoted with alkali metals, silver or lead, and may be supported on silica or alundum. The reaction is conducted at 365° to 450° C. in the presence of oxygen and a co-feed of up to 12 moles $H_2O$ per mole isobutyric acid is needed to generate a catalyst with high activity. In Applied Catalysis A: General, 109 (1994) 135–146, Ai et al. further discussed the role of many different promoters for iron phosphate catalyst and found that the best performance was obtained with $Pb^{2+}$.

In Journal of Catalysis 98, 401–410 (1986), Ai found that $V_2O_5$—$P_2O_5$ binary oxide catalysts were effective for the synthesis of methacrylic acid by oxidative dehydrogenation of isobutyric acid. The selectivity to methacrylic acid was a maximum for catalysts with P/V ratio in the range 1.0 to 1.6 when tested in the temperature range 190° C. to 280° C. Ai also disclosed that these catalysts are selective in the vapor phase aldol condensation of (1) formaldehyde with propionic acid to produce methacrylic acid (Appl. Catal., 36 (1988) 221–230; J. Catal. 124, (1990) 293–296) and (2) formalin with acetic acid to produce acrylic acid (J. Catal. 107, (1987) 201–208).

In Journal of Catalysis 124 (1990) 247–258, Watzenberger et al. describe the oxydehydrogenation of isobutyric acid with heteropolyacid catalysts, such as $H_5PMo_{10}V_2O_{40}$.

In U.S. Pat. No. 4,442,307, Lewis et al. disclose a process for the preparation of formaldehyde by oxidizing dimethyl ether in the presence of a catalyst comprising oxides of bismuth, molybdenum and iron. Table 1 of said patent provides the only illustrative Examples at 500° C. in which a 54%Bi-24%Mo-2%Fe catalyst afforded 42% conversion and 46% formaldehyde selectivity while a 55%Bi-25%Mo catalyst gave 32% conversion and 28% formaldehyde selectivity.

Selective catalytic C—C bond formation on MgO to produce α,β-unsaturated compounds was described by Korukawa et al. (Heterogeneous Catalysis and Fine Chemicals, Guisnet et al. Eds., Elsevier Science Publishers, 1988, 299–306). The authors claim to have developed a novel synthetic route by using MeOH as a methylenylating agent. The synthetic method uses magnesium oxide catalysts activated by transition metal cations to produce formaldehyde. According to the authors, "methyl or methylene groups at α-position of saturated ketones, esters or nitrites are converted to vinyl groups by the C—C bond formation using methanol as a $CH_2$= source." The reaction of methyl propionate with methanol over manganese-promoted MgO afforded 10% conversion of methyl propionate and produced 60% methyl methacrylate (MMA), 18% methyl isobutyrate (MIB) and 22% ketones. The reaction occurs at 400° C. in the absence of $O_2$ and co-produces $H_2$ and $H_2O$.

Despite the foregoing developments, it would be desirable to provide a low cost, ethylene-based route through propionic acid to methyl methacrylate employing catalysts that can operate at low temperatures to avoid excessive oxidation of the methylating agent to carbon oxides.

In addition, it would be desirable to provide a method for methylating a carbon adjacent to an electron withdrawing group.

All references cited herein are incorporated herein by reference in their entireties.

BRIEF SUMMARY OF THE INVENTION

The invention provides a process for methylating an alpha carbon adjacent to an electron withdrawing group, said process comprising providing a molecule containing said alpha carbon and said electron withdrawing group, and reacting said molecule in a presence of an acid catalyst with dimethyl ether to substitute a methyl group on said alpha carbon.

In preferred embodiments, said reacting is represented by Equation I:

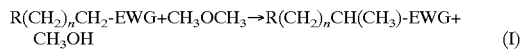

where EWG is said electron withdrawing group, and R is H when n is 0, 1 or 2, and R is alkyl, EWG or aryl when n>2.

In embodiments wherein the electron withdrawing group is an acid, the process can further comprise forming a methyl ester by esterifying said electron withdrawing group with methanol liberated from said dimethyl ether.

In preferred embodiments the process further comprises dehydrogenating said methyl group in a presence of an oxidant to produce an α,β-unsaturated bond in said molecule, as represented by Equation II:

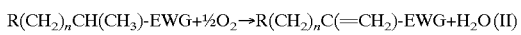

where EWG is said electron withdrawing group, and R is H when n is 0, 1 or 2, and R is alkyl, EWG or aryl when n>2.

BRIEF DESCRIPTION OF SEVERAL VIEWS OF THE DRAWINGS

Not applicable.

DETAILED DESCRIPTION OF THE INVENTION

The present invention relates to the use of dimethyl ether or dimethyl ether and oxygen as feedstocks to introduce a methyl group or carbon-carbon double bond on a carbon adjacent to an electron withdrawing group using a particular class of catalysts. Dimethyl ether can be used to methylate an alpha-carbon adjacent to an electron withdrawing group. The inserted methyl group can be oxidatively dehydrogenated with oxygen or other oxidant over said catalyst in the same process step to form alpha,beta-unsaturated compounds. When the electron withdrawing group is an acid, the liberated methanol from the dimethyl ether can be used to esterify the acid to form a methyl ester.

The subject invention can be successfully applied to feedstocks of intermediate compounds which contain various electron withdrawing groups. Said compounds can be represented by the molecular formula $R(CH_2)_nCH_2$-EWG, where EWG is an electron-withdrawing-group, such as an acid, ester, or nitrile, and R is H when n is 0, 1 or 2, otherwise R is alkyl, EWG or aryl. General examples include such intermediate compounds as carboxylic acids, carboxylic acid esters, nitrites, aromatic ring and ketones. Specific examples include acetic acid, propionic acid, methyl acetate, methyl propionate, acetonitrile, propionitrile, acetone, and other compounds containing these structural units.

The products formed using the present invention contain additionally one carbon atom attached to the carbon next to EWG on the corresponding intermediate compound as feedstock. These products fall into two categories depending on whether or not oxygen or another oxidant is contained in the feedstock with the dimethyl ether.

In the absence of oxygen (or other oxidant) in the feedstock, a methyl group is added from dimethyl ether to the alpha-carbon of the acid, ester, nitrile or ketone, to produce the corresponding saturated compound. General examples include products with the formula $R(CH_2)_nCH(CH_3)EWG$, where EWG and R are as defined above. Specific examples include the formation of propionic acid from acetic acid, isobutyric acid from propionic acid, methyl propionate from methyl acetate, methyl isobutyrate from methyl propionate, propionitrile from acetonitrile, isobutyronitrile from propionitrile, and methyl ethyl ketone from acetone. The general reaction is described by the following equation:

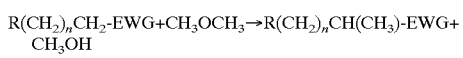

where EWG is CN, COR or COOR and R is H or $CH_3$.

When the feedstock contains oxygen, the methyl group added from dimethyl ether to the alpha-carbon of the acid, ester, nitrile or ketone is dehydrogenated to produce the corresponding alpha,beta-unsaturated compound. General examples include products with the formula $R(CH_2)_nC(=CH_2)EWG$, where EWG is an electron-withdrawing-group, such as an acid, ester, or nitrile, and R is H when n is 0, 1 or 2, otherwise R is alkyl, EWG or aryl. Specific examples include the formation of acrylic acid from acetic acid, methacrylic acid from propionic acid, methyl acrylate from methyl acetate, methyl methacrylate from methyl propionate, acrylonitrile from acetonitrile, methacrylonitrile from propionitrile, and methyl vinyl ketone from acetone. The general reaction is described by the following equation:

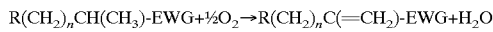

$$R(CH_2)_nCH(CH_3)\text{-}EWG+\tfrac{1}{2}O_2 \rightarrow R(CH_2)_nC(=CH_2)\text{-}EWG+H_2O$$

where EWG is CN, COR or COOR, and R is H or $CH_3$.

The exact mechanism for addition of the methylene group to produce unsaturated products is not known. In one proposed mechanism, the saturated compound produced when a methyl group is added to the alpha-carbon of the acid, ester, nitrile or ketone is dehydrogenated with oxygen in-situ to produce the corresponding alpha,beta-unsaturated compound. In another proposed mechanism, the dimethyl ether is dehydrogenated with oxygen to form formaldehyde which adds in an aldol condensation mechanism to the alpha-carbon of the acid, ester, nitrile, or ketone to produce the corresponding alpha,beta-unsaturated compound. This latter mechanism is least likely because the observed product slate contains the methylated intermediate. The present invention makes no distinction between these two mechanisms.

Researchers have not recognized that dimethyl ether can be an excellent methylating agent because of its cost and because the low temperature activation of dimethyl ether to selectively produce formaldehyde was not previously known.

In embodiments of the present invention, said catalysts may be used in stages such that in the first stage a saturated compound is produced in the absence of oxygen, then in a second stage the saturated compound is oxidatively dehydrogenated to produce the particular alpha,beta-unsaturated product.

In embodiments of the present invention, when the feedstock is a carboxylic acid, the dimethyl ether, or the liberated methanol from the dimethyl ether subsequent to methylation, can esterify the product acid to form the corresponding methyl ester. This reaction of a carboxylic acid with dimethyl ether or methanol is a well-known acid catalyzed organic reaction. For reasons of product handling, storage and use the esters are the preferred commercial product and these compounds are currently prepared in additional process steps using sulfuric acid or acidic ion exchange resins as catalysts. In the present invention, when dimethyl ether is used as feedstock for methylating an alpha-carbon next to an electron withdrawing group, the methanol co-product readily esterifies the product acid at the elevated temperatures and gas phase conditions where the present invention operates. In a specific example of the instant invention, dimethyl ether, propionic acid and oxygen are used as feedstock over the catalysts described herein to give methyl methacrylate product.

The process of this invention uses dimethyl ether and oxygen (e.g., oxygen gas, air or oxygen-enriched air) to introduce a carbon-carbon double bond on a carbon adjacent to an electron withdrawing group of an intermediate under conditions sufficient to effect methylation and dehydrogenation, said feedstock comprising an intermediate carboxylic acid, ester, nitrile or ketone depending on available feeds and desired product. An example of an intermediate carboxylic acid is propionic acid. Typically, the dimethyl ether/propionic acid (DME/PA) ratio will range from about 0.5 to about 20 and the $DME/O_2$ ratio will range from about 1 to about 25. Reaction temperatures range from about 150° C. to 500° C., but are preferably from 250° C. to 400° C. Reaction pressures may vary, but typically range from 0 to 50 psig. Total feed space velocities vary from about 100 to 5000 $hr^{-1}$, preferably 200 to 2000 $hr^{-1}$. Gas Hourly Space Velocity (GHSV) is defined as the total feed rate in $cm^3$ gas at STP/hr ratioed to the catalyst bed volume in $cm^3$. The resulting conversion of DME generally will range from about 10% to 80% with total selectivity to all desirable products greater than 60%. Desirable products include all those compounds produced in the process which are themselves already defined as intermediate feedstocks and therefore can be recycled or optimized by process variables.

A key to the process of the present invention, which uses dimethyl ether and oxygen as feedstocks to introduce a carbon-carbon double bond on a carbon adjacent to an electron withdrawing group of an intermediate carboxylic acid, ester, nitrite or ketone, resides in the use of the particular catalyst system. The prior art that teaches the use of methanol feedstock to alkylate these intermediates discloses the use of basic oxide catalyst supports, such as MgO. The prior art that teaches the use of formaldehyde feedstock to alkylate the intermediate compounds require the use of partial oxidation catalysts such as $V_2O_5$—$P_2O_5$. We have found that while some additional benefit may be realized by the use of selected partial oxidation catalysts, pure or supported, only certain partial oxidation catalyst functionalities are effective.

Thus, catalysts particularly suitable for use in the present invention include Lewis acid catalysts, combined Lewis acid and Brönsted acid catalysts, and Lewis acid or mixed Lewis plus Brönsted acids containing selected partial oxidation catalyst property. Specific, non-limiting examples include gamma-alumina, amorphous silica-alumina, steam-treated zeolites such as ultra-stable Y, acid washed clays, alumina impregnated clays, and $MoO_3$ on gamma-alumina.

The invention will be illustrated in more detail with reference to the following Examples, but it should be understood that the present invention is not deemed to be limited thereto.

EXAMPLES

The process for carrying out the methylation reactions is similar to the processes used in the prior art, except for (among other things) the substitution of dimethyl ether for formaldehyde and the preferred catalysts of this invention. Catalyst performance was determined using a down-flow, heated packed bed reactor system. The reactor tube was 0.5" (1.3 cm) o.d. with a 0.049" (0.12 cm) wall thickness. To ensure that a single vapor phase feed was passed through the catalyst bed the liquid feed, as well as the DME, air, and nitrogen co-feeds were all pre-heated by passing each feed through a length of coiled 0.125" (0.32 cm) o.d. tubing heated and maintained at 200° C. Further, the feeds were combined and mixed in the top zone of the reactor tube which contained inert quartz chips. Typically 5.0 $cm^3$ of 20–35 mesh (Tyler Equivalent) of catalyst particles was loaded in the reactor tube which contained a centrally located thermocouple. The catalyst bed was supported in the reactor tube on a small wad of quartz wool followed by more quartz chips which completely filled the tube. The entire reactor tube fit concentrically and snugly into a solid stainless steel block which is heated to maintain a constant temperature zone. The effluent from the reactor was carried in heat traced 0.0625" (0.16 cm) tubing and maintained at 200° C. The reactor pressure was not regulated but was typically between 7 to 10 psig. Samples were analyzed on-line by injecting a 250 microliter gas sample at 180° C. onto a HP 5890 Gas Chromatograph. Organic products were determined using a flame-ionization detector, while inorganic compounds were determined on a thermal conductivity detector. Both detectors were calibrated by molar response factors and $N_2$ was used as an internal standard.

The process of the present invention preferably takes place in the gas phase.

The following parameters are useful to define the process of the invention:

Gas Hour Space Velocity (GHSV)=$cm^3$ feed (STP)/$cm^3$ catalyst/hr=$hr^{-1}$;

% PA Conversion=100×($PA_{in}$-$PA_{out}$)/$PA_{in}$,
where $PA_{in}$ is the mols of PA in the inlet, and $PA_{out}$ is the mols of PA in the outlet;

% DME Conversion=100×($DME_{in}$-$DME_{out}$)/$DME_{in}$,
where $DME_{in}$ is the mols of DME in the inlet, and $DME_{out}$ is the mols of DME in the outlet;

% Carbon Balance=100×(total moles carbon analyzed in effluent),
(3×moles $PA_{in}$+2×moles $DME_{in}$)

For a particular component analyzed in the effluent, the carbon in that component which is derived from PA is used to determine PA-based selectivity.

Therefore, the PA-based selectivity (%S(PAB)) is determined as follows:

%S(PAB)=100×(moles carbon for component)× (multiplier)
(3×moles PA consumed)

Table A below shows the carbon accounting used and gives the "multiplier" for determining the PA-based selectivity. The multiplier (M) is defined as follows:

M=(No. Carbons in PA molecule)/(Carbons in component from PA)
=3/(Carbons in component from PA)

Thus, for acetaldehyde, the "multiplier" is 3/2 or 1.500. For methyl isobutyrate, the multiplier is 3/5 or 0.600 since two of the carbons in the molecule are derived from DME.

Examples 1 and 2

(Gamma-$Al_2O_3$)

Five experiments were conducted using the above described procedure to evaluate gamma-$Al_2O_3$ in the synthesis of methyl methacrylate by oxidative dehydrogenation of propionic acid and dimethyl ether. A sample of ⅛" gamma-$Al_2O_3$ extrudates, CS331-4, was obtained from United Catalysts, Inc. (UCI) and was described by the manufacturer as 99.6% by weight $Al_2O_3$. It had a surface area of 175–275 $m^2$/g and pore volume of 0.6 $cm^3$/g. A portion of this catalyst support was crushed and sieved and 2.87 grams (5.0 $cm^3$) loaded into a reactor tube as described above. In Examples 1 and 2 of Table 1, the temperature was 330° C. and 350° C., respectively. At 350° C., this unmodified gamma-$Al_2O_3$ catalyst which typically has only Lewis acidity, showed 63% conversion of PA and MMA, methacrylic acid (MAA), isobutyric acid (IBA) and MIB of 1.1%, 0.8%, 0.3% and 0.8%, respectively, as well as a MP (methyl propionate) selectivity of 92.0%. This is a very high selectivity to useful products of 95.0%. It has only a low methylation activity at the terminal carbon of 0.1% butyric acid selectivity. At the lower temperature of 330° C., the IBA and MAA selectivities increase to 0.7% and 1.6%, respectively, however, the MMA selectivity decreases to 0.6% and the byproducts, acetaldehyde and diethylketone, both increase significantly.

In Examples 1 and 2, it is shown that the desired products methyl propionate, methyl isobutyrate, methyl methacrylate, isobutyric acid and methacrylic acid are produced using gamma-$Al_2O_3$ catalyst with a combined selectivity at 350° C. of 95.0% at 63% PA conversion and 64% DME conversion. The DME/PA ratio was 0.82 and the DME/$O_2$ ratio was 3.8.

Examples 3, 4 and 5

(Gamma-$Al_2O_3$; Stop $O_2$)

In Examples 3, 4 and 5, the catalyst temperature was set at 330° C. then the flow of air was stopped and the product stream subsequently sampled at three 0.5-hour increments. The reaction conditions and catalytic results are shown in Table 1. Examples 3, 4 and 5 demonstrate that the selectivity to methylation as indicated by IBA and MIB remains unchanged. The examples also show that the selectivity to MMA and MAA are substantially eliminated when oxygen is absent from the feedstock. Compared to Example 1 at 330° C., the methyl propionate selectivity increased to 90–95% apparently because the yield loss to acetaldehyde (ACH) seen in Example 1 was completely eliminated.

Examples 3 to 5 illustrate that when $O_2$ is absent from the feed the dehydrogenated products, such as methyl methacrylate and methacrylic acid, are eliminated or substantially reduced in less than about 1 hour time on stream. The methylated products such as methyl isobutyrate and isobutyric acid are unaffected. The results also show that the byproduct acetaldehyde is dependent on oxygen concentration, a parameter which must be optimized. The catalyst has a selectivity to esterification that is greater than 90%.

Examples 6 and 7

(Gamma-$Al_2O_3$; GHSV, T)

In Example 6, a 2.72 gram (5.0 $cm^3$) sample of gamma-$Al_2O_3$ was loaded into a reactor tube as described above and the $N_2$ and air flows were set to give a 10% $O_2$ concentration. The catalyst temperature was increased to 400° C. and maintained at this temperature for 10 hrs. The catalyst temperature was then set at 350° C. and the PA and DME flows were set to give the GHSV and mole fractions of feed components shown in Table 2. The product stream was analyzed. The DME conversion was very similar to that seen in Example 2; however, the PA conversion increased to 91%, versus 63% in Example 2. The selectivity to MMA was 1.2%. Byproduct acetaldehyde increased to 6.2% at the expense of MP at this lower GHSV of 500 $hr^{-1}$ and DME/PA ratio of 0.83.

In Example 7, at the end of a 6 hour testing period the $N_2$ and air flows were set to give a 10% $O_2$ concentration. The catalyst temperature was increased to 400° C. and maintained at this temperature for 10 hrs. The catalyst temperature was then set at 350° C. and the PA and DME flows were set to give the GHSV and mole fractions of feed components shown in Table 2. The results obtained for Example 7 reproduced those already disclosed for Example 6.

In Examples 6 and 7, it is demonstrated that lower GHSV and higher concentration of the feedstock can result in significant increases in conversion of both PA and DME with moderate changes in the selectivity pattern.

Examples 8, 9 and 10

(Gamma-$Al_2O_3$; DME/PA and DME/$O_2$ Ratios)

The process conditions were varied over the gamma-$Al_2O_3$ catalyst to determine their impact on selectivity to methylated and dehydrogenation products. In Examples 8 to 10, the ratios of DME to PA and/or DME to $O_2$ were varied while keeping the GHSV and temperature constant at 500 hr$^{-1}$ and 350° C., respectively. The catalyst of Example 7 was again heated to 400° C. in a N$_2$/Air blend as before, then set at 350° C. The mole fractions of feed components are shown in Table 3. The product stream was analyzed and the results compared to Example 7, which is repeated in Table 3. For Example 7, the DME/PA ratio was 0.83 and the DME/O$_2$ ratio was 3.8.

In Table 3, the PA partial pressure was decreased while keeping the other feeds constant, that is, DME/PA ratio increased (Example 8 vs. Example 7) and the MMA increased to 1.6% from 1.3% and other methylated products also increased. However, the acetaldehyde and other byproducts returned to the levels seen in Example 7. When O$_2$ concentration was increased (Example 9 vs. Example 8, same PA partial pressure), the MMA decreased to 1.1% but all methylated products increase, in particular MIB almost doubles from 0.7% to 1.3%. The acetaldehyde further increases unacceptably to 7.5% selectivity.

The best result in Table 3 was obtained by operating with a DME/PA ratio of 3.29 and DME/O$_2$ ratio of 7.6 while keeping O$_2$ concentration at the original value of 0.054 mole fraction (Example 10 vs Example 8). The MMA selectivity further increased to 2.8%, MIB was 1.1%, and MP was maintained at 90.8%. Furthermore, the acetaldehyde and diethylketone (DEK) both dropped to the lowest levels over this catalyst of 1.9% and 0.5%, respectively.

In Examples 8, 9 and 10, it is shown that the selectivity to methylated products is significantly increased from PA and DME when the DME/PA ratio is increased from 0.82 to 3.29 and the DME/O$_2$ ratio is simultaneously doubled from 3.8 to 7.6 without any decrease in MP selectivity. At the same time, the selectivity to the principal byproducts acetaldehyde, ethyl propionate and diethylketone are substantially decreased. It is also shown that an increase in O$_2$ partial pressure from 5% to 10% detrimentally affects product selectivity while additionally increasing methyl acetate yield.

Examples 11 and 12
(Gamma-Al$_2$O$_3$; Other Feedstocks)

In Examples 11 and 12 of Table 4, results are shown for conversion of methyl propionate to methyl methacrylate and for acetic acid to methyl acrylate, both compared to propionic acid to MMA. The catalyst of Example 7 was again heated to 400° C. in a N$_2$/Air blend as before, then set at 350° C. The mole fractions of feed components are shown in Table 4. The product stream was analyzed and the results compared to Example 7 which is repeated in Table 4. For Example 7, the DME/PA ratio was 0.83 and the DME/O$_2$ ratio was 3.8. In Example 11 at 350° C., similar GHSV and molar ratios, the MP feed gave a lower conversion of 36% but had MMA and MIB selectivities of 5.9% and 3.3%, respectively. The MP also hydrolyzes to give 41.4% PA selectivity. The acetaldehyde, diethylketone, and methyl acetate byproducts appear to arise primarily from MP, however, from the results of the process variable study in Examples 8 to 10, these byproducts can be minimized. This Example demonstrates that MP is a useful primary or recyclable feed component to produce MMA.

In Example 12 of Table 4, acetic acid does not methylate as readily. However, it affords 99% selectivity to methyl acetate. Apparently, the acetaldehyde and diethylketone seen with the other feedstocks do not arise from acetic acid or methyl acetate intermediates. Thus, as demonstrated by Examples 7 and 10 of Table 3, the acetaldehyde and diethylketone byproducts can be minimized through competitive adsorption by DME.

Example 11 illustrates that MP readily converts to give MMA and MIB with the highest selectivity achieved of 6% and 3%, respectively. This indicates that MP is a preferred feedstock that is more readily methylated than PA. At the low DME/MP ratio of 0.72 and the results demonstrated in Examples 8 to 10 this selectivity can be further increased. Thus, both PA and MP are recyclable feedstocks. The high selectivities to byproducts indicates that the required ratio of O$_2$ to feed components is different for MP and PA feedstocks. In Example 12, it is demonstrated using acetic acid that very little methylation and oxidative dehydrogenation activity is seen. Since the traditional aldol condensation mechanism should be preferred with acetic acid versus PA, it is apparent that the gamma-alumina operates via a different mechanism. It is also confirmed that gamma-alumina is an excellent esterification catalyst when DME is used as feedstock. This feature enhances the observed yield of MMA from PA by producing in situ the preferred MP feedstock.

Examples 13–17
(Comparative Examples; Other Acidic Catalysts)

In Examples 13, 14 and 15 of Table 5, results are shown for conversion of PA to MMA over HZSM-5 catalyst, a strong Brönsted acid. The HZSM-5 catalyst was obtained as silica bound extrudates from United Catalysts, Inc. and had a bulk Si/Al ratio of 62. The Si/Al ratio of the framework as determined using $^{29}$Si MAS-NMR was 45. In these Examples, the catalyst temperature was set at 275° C., 330° C. and 350° C. sequentially without any pre-treatment. The GHSV was 920 hr$^{-1}$ and the temperature and mole fractions of feed components are given in Table 5. The product stream was analyzed and the results are disclosed in Table 5.

The results in Examples 13, 14 and 15 for HZSM-5 show high conversions of both DME and PA. It is a very good esterification catalyst, yielding a high selectivity to MP of 90–96% in the temperature range 275° C. to 350° C. Selectivities to MMA, IBA and MIB of 0.3%, 0.1% and 0.4% were measured at 330° C. The conversion behavior vs. temperature indicates that this strong acid catalyst, which is known to make hydrocarbons from DME or MeOH, may have coked at temperatures above 300° C.

The results in Examples 16 and 17 are for an amorphous Al$_2$O$_3$/SiO$_2$ catalyst with both Lewis and Brönsted acidity. This commercial catalyst contains 13.5% Al$_2$O$_3$ and has a surface area of 130 m$^2$/g. At 330° C., it gave DME and PA conversions of 38% and 23%, respectively. Its selectivity to MP at 330° C. was 70.5%, less than HZSM-5, but it afforded 6.2% MAA, 0.7% IBA and 0.2% MMA. A total of 77.6% useful products were afforded by this catalyst compared to a very high selectivity to useful products of 95.0% for g-Al$_2$O$_3$ in Example 2 at 350° C. and the same flow and partial pressure of components.

In Examples 13 to 15, it is shown that while a typical strong Brönsted acid catalyst is effective for esterification of PA to MP using DME, it shows only little selectivity to methylation. Such a catalyst could, however, be used to first esterify PA in a first layer of a dual layer catalyst bed in which the second layer of catalyst, gamma-alumina, can be used to methylate the MP intermediate. Examples 16 and 17 demonstrate that a mixed Brönsted acid and Lewis acid catalyst, such as silica-alumina, can be used to methylate PA and produce an enhanced, un-optimized selectivity to MAA of 6% at 330° C.

Examples 18 and 19
(10–12% MoO$_3$/Al$_2$O$_3$)

Experiments were conducted to evaluate the effect of transition metal elements on the synthesis of methyl methacrylate by oxidative dehydrogenation of propionic acid and dimethyl ether. A sample of $MoO_3$ on gamma-$Al_2O_3$, T-306, was obtained from United Catalysts Inc., crushed and sieved, and 2.99 grams (5.0 cm$^3$) loaded into a reactor tube. The catalyst surface area was measured to be 220 m$^2$/g and only a strong gamma-alumina phase was detected by XRD analysis. The reactor effluent was analyzed online by gas chromatography. Results are given in Table 6.

In Example 18, the temperature was set at 300° C. and GHSV was 920 hr$^{-1}$. The $MoO_3/Al_2O_3$ catalyst gave 30% conversion of PA and 38% conversion of DME. The catalyst gave a high selectivity to acetaldehyde and acetic acid byproducts of 40.1% and 12.7%, respectively, at 300° C. In Example 19, the catalyst temperature was increased to 350° C. The $MoO_3/Al_2O_3$ catalyst gave 73% PA conversion and afforded the desirable products MMA, MAA, IBA and MIB at 1.1%, 0.7%, 0.2% and 0.7%, respectively, as well as a substantially improved MP selectivity of 84.2%.

The effect of adding molybdenum, a redox transition metal element, to the gamma-alumina catalyst is demonstrated in Examples 18 and 19. Compared to Example 2 at the same GHSV and temperature, it is seen in Example 19 that the $Mo/Al_2O_3$ catalyst is more active and affords a similar slate of methylated products. This catalyst has similar MMA, MAA, MIB and IBA selectivity at a higher conversion than gamma-alumina. The already demonstrated role of $O_2$ in the formation of acetaldehyde and other byproducts indicates that this catalyst should function at a lower $O_2$ concentration.

Example 20
(Preparation of K-treated 10–12% $MoO_3/Al_2O_3$)

3.75 gms of potassium acetate from Aldrich was added to de-ionized $H_2O$ and dissolved up to 20.0 mL. A 25.0 gram sample of the T-306 catalyst extrudates described in Example 18 was weighed then the potassium acetate solution added dropwise to the T-306 extrudates to incipient wetness. The extrudates were allowed to dry at room temperature for 24 hrs. The catalyst sample was then calcined as extrudates in air at 500° C. for 6 hrs. The surface area was 211 m$^2$/g and XRD analysis showed only a strong γ-$Al_2O_3$ phase. Elemental analysis gave 6.09 wt % potassium giving a K/Mo ratio of 2.20. The K/Mo ratio is slight above 2 to yield $K_2MoO_4$ with some K passivating the acidity of the gamma-$Al_2O_3$ support.

Examples 21 and 22
(K-treated 10–12% $MoO_3/Al_2O_3$)

A sample of the potassium-treated $MoO_3$ on gamma-$Al_2O_3$ prepared in Example 20 was crushed and sieved, and 2.98 grams (5.0 cm$^3$) loaded into a reactor tube. The reactor temperature was then increased to 300° C., the GHSV set at 920 hr$^{-1}$ and the effluent was analyzed. Results are given in Table 6.

In Example 21, the catalyst gave 23% conversion of PA and 14% DME conversion. This catalyst gave almost exclusively acetaldehyde at 81.8% selectivity and diethylketone at 15.9% selectivity. The 2.3% IBA selectivity was about the same compared to the untreated T-306 catalyst at the same temperature. No MMA or MAA was observed. In Example 22, the catalyst temperature was increased to 330° C. and the PA conversion was 17%. The MP selectivity was only 5.4% and IBA but IBA increased to 4.0%. The combined acetaldehyde and diethylketone byproduct selectivity was 90.5%. This catalyst also had a high $CO_2$ make of 60.5% based on DME.

In Examples 21 and 22, it is shown that base treatment of the $Mo/Al_2O_3$ catalyst substantially decreases conversion and completely reverses the product slate to make the undesirable acetaldehyde and diethylketone the overwhelmingly dominant products.

Example 23
(Preparation of $TiO_2/Al_2O_3$ Catalyst)

A 50 wt % solution of titanium bis(ammonium lactato) dihydroxide in water with a density of 1.222 grams/mL was obtained from Aldrich. 51.03 grams of the titanium complex was added to a 100 mL polypropylene bottle. A 24.96 gram sample of the CS331-4 gamma-alumina extrudates with 0.6 cm$^3$/g pore volume used in Example 1 was weighed out. The alumina extrudates sample was then added to the excess titanium solution in the polypropylene bottle until evolution of air from the pores stopped to give a sample with estimated 9.0 wt % $TiO_2$. The bottle was then capped and the bottle swirled to gently mix the contents without degrading the extrudates. The extrudates were in contact with the solution for a total of 30 minutes after which the solution was filtered off and the extrudes put into a nitrogen purged muffle furnace at 110° C. for 2 hours. The temperature of the catalyst sample was then increased to 400° C. in nitrogen and after 1 hour the purge was changed to air. After an additional 1 hour at 400° C., the extrudates were calcined in air at 600° C. for 15 hours.

Example 24
($TiO_2/Al_2O_3$ Catalyst)

A portion of the $TiO_2$ on gamma-$Al_2O_3$ prepared in Example 23 was crushed and sieved, and 2.97 grams (5.0 cm$^3$) loaded into a reactor tube. The reactor temperature was then increased to 350° C., the GHSV set at 920 hr$^{-1}$ and the effluent was analyzed. Results are given in Table 7.

In Example 24, the catalyst temperature was set to 350° C. and the PA conversion was determined to be 12%. The MP selectivity was only 36.6% and IBA was 1.7%. The catalyst had a high selectivity for acetaldehyde, diethylketone and acetic acid byproducts. The unmodified gamma-$Al_2O_3$ catalyst in Example 2, which typically has only Lewis acidity, showed 63% conversion of PA and MMA, MAA, IBA and MIB of 1.1%, 0.8%, 0.3% and 0.8%, respectively, as well as a MP selectivity of 92.0%. The $Ti/Al_2O_3$ catalyst shows high byproduct at low conversion, which is not beneficial.

Example 25
(Preparation of $MoO_3/TiO_2/Al_2O_3$ Catalyst)

13.95 grams of ammonium hepta-molybdate tetrahydrate salt was dissolved in 36.2 grams deionized water to give an approximate 28% solution. A 17.84 gram sample of the $TiO_2/Al_2O_3$ extrudates prepared in Example 23 was weighed out then added to the excess molybdate solution until evolution of air from the pores stopped. The contents were swirled to gently mix for a total of 5 minutes after which the solution was filtered off and the extrudes put into an air purged muffle furnace at 110° C. for 2 hours. The temperature of the catalyst sample was then increased to 400° C. in air and held for 2 hours to give a sample with estimated 12 wt % $MoO_3$ content.

Example 26
($MoO_3/TiO_2/Al_2O_3$ Catalyst)

A portion of the $MoO_3$ on $TiO_2/Al_2O_3$ extrudates prepared in Example 25 was crushed and sieved, and 3.50 grams (5.0 cm$^3$) loaded into a reactor tube. The reactor temperature was then increased to 350° C., the GHSV set at 920 hr$^{-1}$ and the effluent was analyzed. Results are given in Table 7. The PA conversion was determined to be 39%. The MP selectivity was 53.9% and MAA and IBA were 1.1% and 0.4%, respectively. Like the $MoO_3/Al_2O_3$ commercial T-306 catalyst in Example 18, this $MoO_3/TiO_2/Al_2O_3$ catalyst gave 3.1% acrylic acid.

The combination of Mo and Ti on $Al_2O_3$ in Example 26 affords no additional value to the $Mo/Al_2O_3$ of Example 18. While the byproducts are reduced at similar conversions, it does not afford any MMA and still produces acrylic acid.

Example 27
(Preparation of $Bi_6Mo_2O_{15}$ Catalyst)

36.99 grams of bismuth (III) oxide and 7.60 grams of molybdenum trioxide were mixed and then ball milled for 8 hours. The mixture was heated at 110° C. for 15 hours then calcined in nitrogen at 600° C. for 20 hours. After cooling under nitrogen, the solid was ground into a fine powder. XRD analysis identified $Bi_6Mo_2O_{15}$ as the major phase, with $Bi_2MoO_6$ and $Bi_{38}Mo_7O_{78}$ as moderate phases.

Examples 28 and 29
($Bi_6Mo_2O_{15}$ Catalyst)

A portion of the $Bi_6Mo_2O_{15}$ catalyst prepared in Example 27 was pelletized then crushed and sieved, and 16.06 grams (5.0 cm$^3$) loaded into a reactor tube. In Example 28, the reactor temperature was increased to 300° C., the GHSV set at 920 hr$^{-1}$ and the effluent was analyzed. Results are given in Table 7. The PA conversion was determined to be 37%. The MP selectivity was only 0.5% and IBA was 2.0%. The catalyst had a high selectivity for acetaldehyde and diethylketone byproducts of 62.3% and 35.2%, respectively.

In Example 29, the reactor temperature was increased to 350° C., the GHSV kept at 920 hr$^{-1}$ and the effluent was analyzed. The PA conversion was determined to be 39%. The MP selectivity only increased to 2.5% and IBA was 1.8%. The catalyst maintained a high selectivity for acetaldehyde and diethylketone byproducts of 88.1% and 7.7%, respectively.

In Examples 28 and 29, a partial oxidation catalyst, $Bi_6Mo_2O_{15}$, is evaluated. This catalyst produces high byproducts including $CO_2$.

Comparative Examples 30 and 31
($FePO_4$)

Experiments were conducted to evaluate catalyst compositions which are known to be effective for oxidative dehydrogenation of IBA to MAA in the synthesis of methyl methacrylate from propionic acid and dimethyl ether. A sample of $FePO_4 \cdot 2H_2O$ was obtained from Aldrich. The powder was pelletized, crushed and sieved, and 4.52 grams (5.0 cm$^3$) loaded into a reactor tube. The reactor effluent was analyzed online by gas chromatography. Results are given in Table 8. In Example 18, the temperature was set at 300° C. and GHSV was 920 hr$^{-1}$. The $FePO_4$ catalyst gave 35% conversion of PA and 34% conversion of DME. The catalyst gave a high selectivity to acetaldehyde and acetic acid byproducts of 66% and 17%, respectively, at 300° C. In Example 30, the catalyst temperature was increased to 330° C. The $FePO_4$ catalyst gave only 17% PA conversion and afforded the desirable product IBA with 1.3% selectivity, as well as a substantial acetaldehyde selectivity of 53.5%. The oxidative dehydrogenation activity of this catalyst is seen in its selectivity to acrylic acid of 2.7% at 300° C. and 8.4% at 330° C.

Example 32
(Preparation of 1% $V_2O_5/SiO_2$ Catalyst)

25.1 grams Cabosil grade L90 $SiO_2$ were added to a 600 mL beaker. Then, 0.4016 grams $NH_4VO_3$ from Aldrich was added to a 120 mL wide mouth glass bottle containing 25 mL deionized $H_2O$. Citric acid (0.2145 grams) was then added and mixed well. Deionized $H_2O$ was then added to 40 mL, and the bottle was placed in a water bath at 60° C. to dissolve residue. The solution was cooled to ambient to ambient temperature. The resulting solution of $NH_4VO_3$ was added dropwise to the $SiO_2$ while mixing the powder to incipient wetness. The sample was dried for 1 hour at 115° C. then for 1 hour at 300° C. The sample was then calcined at 500° C. for 18 hrs after which it was cooled to ambient temperature.

Comparative Examples 33 and 34
(1% $V_2O_5/SiO_2$ Catalyst)

Experiments were conducted to evaluate catalyst compositions containing vanadium, which is known to be effective for oxidative dehydrogenation of IBA to MAA in the synthesis of methyl methacrylate from propionic acid and dimethyl ether. A sample of the catalyst chunks from Example 32 was crushed and sieved, and 1.46 grams (5.0 cm$^3$) loaded into a reactor tube. The reactor effluent was analyzed online by gas chromatography. Results are given in Table 8. In Example 33, the temperature was set at 300° C. and GHSV was 920 hr$^{-1}$. The 1% $V_2O_5/SiO_2$ catalyst gave 30% conversion of PA and 23% conversion of DME. The catalyst gave a high selectivity to acetaldehyde, ethyl propionate, diethylketone and acetic acid byproducts at 300° C. In Example 34, the catalyst temperature was increased to 330° C. The 1% $V_2O_5/SiO_2$ catalyst gave 20% PA conversion and maintained a substantial byproduct selectivity. The oxidative dehydrogenation activity of this catalyst is seen in its selectivity to acrylic acid of 1.3% at 330° C.

Example 35
(Preparation of V—Si—P Catalyst)

50 mL of deionized water was added to each of two 200 mL beakers. To one beaker was added 12 mL of 85% lactic acid from Aldrich. To the other beaker was added 33.24 grams of 85% $H_3PO_4$. Both beakers were heated to 60° C. while stirring with Teflon coated stir bars. 11.69 grams of $NH_4VO_3$ was added to the hot lactic acid solution and the temperature further increased to 80° C. until a violet blue solution was obtained. 201.33 grams of colloidal silica solution from Aldrich (DuPont Ludox SM-30) was added to a 2000 mL beaker and stirred with a stir bar. The hot lactic acid and phosphoric acid solutions were then added simultaneously in approximately 1 minute to the colloidal silica solution. This mixture was then heated to 60° C. while stirring and a nitrogen purge was bubbled into the mixture to evaporate. After 3 hours the solution became gel-like and the beaker was left on low heat to evaporate overnight into a solid cake. The solid cake was further dried in a muffle furnace at 200° C. for 15 hours. A portion of the solid was crushed and sieved then calcined at 400° C. in air flow for 15 hours.

Comparative Example 36
(V—Si—P Catalyst)

A 3.68 gram (5.0 cm$^3$) sample of the calcined catalyst from Example 35 was loaded into a reactor tube. The temperature was set at 350° C. and GHSV was 920 hr$^{-1}$. The reactor effluent was analyzed online by gas chromatography. Results are given in Table 8. The V—Si—P catalyst gave 65% conversion of PA and 59% conversion of DME. The catalyst gave a high selectivity of 90% to MP and only 0.1% IBA. Acetaldehyde was the dominant byproduct at 7.9%.

Comparative Examples 30–31, 33–34 and 36 demonstrate that typical state of the art catalysts for IBA oxidative dehydrogenation or aldol condensation of PA with formaldehyde are not effective for making MMA.

Examples 37A–37C and 38A–38B
(Gamma-$Al_2O_3$; DME/MP & DME/$O_2$ Ratios)

The fact that MP can be methylated with DME to give MMA and MIB is a key experimental observation already described in Example 11 of the current application. The following results expand upon Example 11. MP can be a recyclable product in a process which utilizes PA feedstock, the MP originating from either a primary esterification of PA with DME or a secondary esterification of PA with co-product MeOH. Alternatively, PA is a recyclable product in a process which utilizes MP as feedstock, the PA arising from in situ hydrolysis of MP with co-product $H_2O$. The following reaction most likely has a finite equilibrium constant (Keq) in the temperature range of interest:

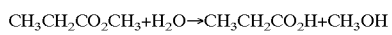

$CH_3CH_2CO_2CH_3 + H_2O \rightarrow CH_3CH_2CO_2H + CH_3OH$

Thus, in preferred embodiments, the optimum feedstock in a MMA process is a mixture of PA and MP.

The process conditions were varied over gamma-$Al_2O_3$ catalyst to determine their impact on selectivity to methylated and dehydrogenation products using MP as starting feedstock. In these examples, the temperature was maintained at 350° C. and the DME/MP ratio was held at 4.0. A very significant effect of both GHSV and DME/$O_2$ ratio can be seen. Results are shown in Table 9 below. The data show that substantial amounts of useful products are made. For example, in Example 38A, 22.7% MMA, 2.8% MAA, 6.5% MIB and 1.7% IBA are produced when MP is used. Simultaneously, the largest co-product is PA at 42.6% which is recyclable.

The hydrolysis of MP to PA is a reaction which occurs with high selectivity. Since it has already been shown that PA can be directly methylated, and since the reverse reaction (i.e., esterification of PA to MP) is a commercial process with yields of 98–99%, the PA can therefore be subtracted from the total MP conversion and a "single-pass" conversion to methylation and byproducts derived. This "single-pass" conversion is calculated as (Total MP Conversion)×(100-%PA) using the data in Table 9. Since the PA co-product is recyclable, a corresponding "single-pass" selectivity to methylation can then be calculated. Using this approach, the data in Table 9 are summarized in Table 10 (showing the effect of GHSV on "single-pass" MP conversion and selectivity) and Table 11 (showing the effect of DME/$O_2$ on "single-pass" MP conversion and selectivity) below.

At a DME/$O_2$ ratio of 7.6 and GHSV=500 $hr^{-1}$ the %MMA+%MAA obtained is 27.5% and the %MIB+%IBA is 10.9%. By increasing the GHSV from 500 to 920 $hr^{-1}$ at a constant DME/$O_2$ of 7.6, the %MMA+%MAA increased to 36.1% and the %MIB+%IBA decreased to 9.4%, or a combined methylation selectivity of 45%. The acetaldehyde and DEK selectivities are 21.7% and 3.1%, respectively.

In Table 11, when the GHSV was maintained at 920 $hr^{-1}$ but the DME/$O_2$ ratio increased to 20.6 (by decreasing the $O_2$ concentration to 2% from 5%) the best result was obtained: %MMA+%MAA of 49.2% and %MIB+%IBA of 15.8%, or a combined 65% methylation selectivity. Furthermore, the acetaldehyde selectivity dropped to 0%. No acetaldehyde was detected.

Decreasing the GHSV to 500 $hr^{-1}$ while maintaining the DME/$O_2$ at 20.7 resulted in a decrease in "single-pass" conversion, loss of methylation selectivity, and return of acetaldehyde to 25% selectivity.

It is evident from Table 9, Examples 37A and 37C, that the hydrolysis product, propionic acid, increased from 37.2% to 51.4% when the GHSV was increased from 500 to 920 $hr^{-1}$ and the total conversion of MP was constant at 24%. It is apparent that the byproduct acetaldehyde results from reaction of the strongly adsorbing PA product. By increasing the GHSV, the PA (resulting from hydrolysis) is swept from the reactor before it can be decomposed.

While the invention has been described in detail and with reference to specific examples thereof, it will be apparent to one skilled in the art that various changes and modifications can be made therein without departing from the spirit and scope thereof.

TABLE A

| Molecule | Carbons from PA | Multiplier |
| --- | --- | --- |
| CO | 0 | 0.000 |
| CH4 | 0 | 0.000 |
| CO2 | 0 | 0.000 |
| DME | 0 | 0.000 |
| methyl formate | 0 | 0.000 |
| MeOH | 1 | 0.000 |
| acetaldehyde | 2 | 1.500 |
| methyl acetate | 2 | 1.000 |
| EtOH | 2 | 1.500 |
| acetic acid | 2 | 1.500 |
| propanal | 3 | 1.000 |
| acetone | 3 | 1.000 |
| methyl propionate | 3 | 0.750 |
| methyl isobutyrate | 3 | 0.600 |
| methyl acrytate | 3 | 0.750 |
| ethyl propionate | 3 | 0.600 |
| methyl butyrate | 3 | 0.600 |
| methyl methacrylate | 3 | 0.600 |
| propionic acid | 3 | 1.000 |
| isobutyric acid | 3 | 0.750 |
| butyric acid | 3 | 0.750 |
| acrylic acid | 3 | 1.000 |
| methacrylic acid | 3 | 0.750 |
| diethylketone | 5 | 1.200 |

TABLE 1

| Example No. | 1 | 2 | 3 | 4 | 5 |
| --- | --- | --- | --- | --- | --- |
| Catalyst | g-Al2O3 | g-Al2O3 | g-Al2O3 | g-A1203 | g-Al2O3 |
| Temperature, ° C. | 330 | 350 | 330 | 330 | 330 |
| GHSV, hr-1 | 920 | 920 | 920 | 920 | 920 |
| Mol. Frac. DME | 0.2063 | 0.2063 | 0.2063 | 0.2063 | 0.2063 |
| Mol. Frac. PA | 0.2513 | 0.2513 | 0.2513 | 0.2513 | 0.2513 |
| Mol. Frac. O2* | 0.0542 | 0.0542 | 0 | 0 | 0 |

TABLE 1-continued

| Example No. | 1 | 2 | 3 | 4 | 5 |
|---|---|---|---|---|---|
| | Conversion | Conversion | Conversion | Conversion | Conversion |
| % DME | 56 | 64 | 65 | 44 | 51 |
| % PA | 43 | 63 | 36 | 34 | 49 |
| | Selectivity | Selectivity | Selectivity | Selectivity | Selectivity |
| % C, DME-based | | | | | |
| CO | 4.4 | 10.0 | 0.7 | 0.0 | 0.0 |
| CH4 | 0.0 | 0.0 | 0.0 | 0.0 | 0.0 |
| CO2 | 7.7 | 7.2 | 1.0 | 4.4 | 3.0 |
| MeOH | 1.9 | 3.2 | 1.4 | 1.5 | 2.3 |
| methyl formate | 0.0 | 0.0 | 0.0 | 0.0 | 0.0 |
| % C, PA-based | | | | | |
| methyl propionate | 82.5 | 92.0 | 92.9 | 90.2 | 94.8 |
| methyl isobutyrate | 0.7 | 0.8 | 0.5 | 0.5 | 0.6 |
| acetone | 0.0 | 0.0 | 0.0 | 0.0 | 0.0 |
| methyl methacrylate | 0.6 | 1.1 | 0.3 | 0.0 | 0.0 |
| propanal | 0.0 | 0.0 | 0.0 | 0.0 | 0.0 |
| isobutyric acid | 0.7 | 0.3 | 0.7 | 0.6 | 0.5 |
| butyric acid | 0.0 | 0.1 | 0.0 | 0.0 | 9.0 |
| methacrylic acid | 1.6 | 0.8 | 1.7 | 0.1 | 0.1 |
| acrylic acid | 0.0 | 0.1 | 0.2 | 0.0 | 0.0 |
| acetaldehyde | 8.1 | 2.6 | 0.0 | 0.0 | 0.0 |
| methyl acetate | 0.3 | 1.4 | 0.6 | 0.5 | 0.7 |
| ethyl propionate | 0.0 | 0.1 | 0.0 | 0.0 | 0.0 |
| diethylketone | 3.5 | 1.7 | 2.5 | 7.2 | 2.9 |
| acetic acid | 2.0 | 0.9 | 0.7 | 0.9 | 0.4 |
| Total Carbon Balance | 89.7 | 101.8 | 90.2 | 97.1 | 88.6 |

*Balance is $N_2$, i.e., Mole Fraction (DME + PA + $O_2$ + $N_2$) = 1.0

TABLE 2

| Example No. | 6 | 7 |
|---|---|---|
| Catalyst | g-Al2O3 | g-Al2O3 |
| Heated @ 400 C. in 10% O2 | YES | YES |
| Temperature, °C. | 350 | 350 |
| GHSV, hr-1 | 500 | 500 |
| Mol. Frac. DME | 0.2068 | 0.2068 |
| Mol. Frac. PA | 0.2495 | 0.2495 |
| Mol. Frac. O2* | 0.0544 | 0.0544 |
| DME/PA Ratio | 0.83 | 0.83 |
| DME/O2 Ratio | 3.8 | 3.8 |
| | Conversion | Conversion |
| % DME | 63 | 60 |
| % PA | 91 | 92 |
| | Selectivity | Selectivity |
| % C, DME-based | | |
| CO | 7.3 | 6.4 |
| CH4 | 0.0 | 0.0 |
| CO2 | 11.2 | 9.5 |
| MeOH | 5.1 | 5.4 |
| methyl formate | 0.0 | 0.0 |
| % C, PA-based | | |
| methyl propionate | 89.0 | 88.1 |
| methyl isobutyrate | 0.3 | 0.5 |
| acetone | 0.0 | 0.1 |
| methyl methacrylate | 1.2 | 1.3 |
| propanal | 0.1 | 0.1 |
| isobutyric acid | 0.0 | 0.1 |
| butyric acid | 0.0 | 0.0 |
| methacrylic acid | 0.0 | 0.0 |
| acrylic acid | 0.0 | 0.0 |
| acetaldehyde | 6.2 | 6.6 |
| methylacetate | 1.2 | 1.2 |
| ethyl propionate | 0.1 | 0.1 |
| diethylketone | 1.8 | 2.0 |
| acetic acid | 0.0 | 0.0 |
| Total Carbon Balance | 83.9 | 74.0 |

*Balance is $N_2$, i.e., Mole Fraction (DME + PA + $O_2$ + $N_2$) = 1.0

TABLE 3

| Example No. | 7 | 8 | 9 | 10 |
|---|---|---|---|---|
| Catalyst | g-Al2O3 | g-Al2O3 | g-Al2O3 | g-Al2O3 |
| Heated @ 40° C. in 10% O2 | YES | YES | YES | YES |
| Temperature, °C. | 350 | 350 | 350 | 350 |
| GHSV, hr-1 | 500 | 500 | 500 | 500 |
| Mol. Frac. DME | 0.2068 | 0.2064 | 0.2064 | 0.4126 |
| Mol. Frac. PA | 0.2495 | 0.1253 | 0.1254 | 0.1254 |
| Mol. Frac. O2* | 0.0544 | 0.0543 | 0.1 | 0.0543 |
| DME/PA Ratio | 0.83 | 1.65 | 1.65 | 3.29 |
| DME/O2 Ratio | 3.8 | 3.8 | 2.06 | 7.6 |
| | Conversion | Conversion | Conversion | Conversion |
| % DME | 60 | 52 | 59 | 35 |
| % PA | 92 | 94 | 82 | 91 |

TABLE 3-continued

| Example No. | 7 | 8 | 9 | 10 |
|---|---|---|---|---|
| | Selectivity | Selectivity | Selectivity | Selectivity |
| % C, DME-based | | | | |
| CO | 6.4 | 8.2 | 14.2 | 11.5 |
| CH4 | 0.0 | 0.0 | 0.0 | 0.0 |
| CO2 | 9.5 | 12.9 | 17.9 | 12.9 |
| MeOH | 5.4 | 5.7 | 6.2 | 6.8 |
| methyl formate | 0.0 | 0.0 | 0.0 | 0.0 |
| % C, PA-based | | | | |
| methyl propionate | 88.1 | 86.1 | 82.4 | 90.8 |
| methyl isobutyrate | 0.5 | 0.7 | 1.3 | 1.1 |
| acetone | 0.1 | 0.2 | 0.3 | 0.4 |
| methyl methacrylate | 1.3 | 1.6 | 1.1 | 2.8 |
| propanal | 0.1 | 0.2 | 0.2 | 0.1 |
| isobutyric acid | 0.1 | 0.1 | 0.3 | 0.1 |
| butyric acid | 0.0 | 0.1 | 0.2 | 0.1 |
| methacrylic acid | 0.0 | 0.2 | 0.2 | 0.0 |
| acrylic acid | 0.0 | 0.0 | 0.0 | 0.0 |
| acetaldehyde | 6.6 | 7.3 | 7.5 | 1.9 |
| methylacetate | 1.2 | 2.4 | 5.1 | 1.8 |
| ethyl propionate | 0.1 | 0.0 | 0.1 | 0.0 |
| diethylketone | 2.0 | 1.0 | 1.3 | 0.5 |
| acetic acid | 0.0 | 0.0 | 0.0 | 0.0 |
| Total Carbon Balance | 74.0 | 80.0 | 86.8 | 79.5 |

*Balance is $N_2$, i.e., Mole Fraction (DME + PA + $O_2$ + $N_2$) = 1.0

TABLE 4

| Example No. | 7 | 11 | 12 |
|---|---|---|---|
| Catalyst | g-Al2O3 | g-Al2O3 | g-Al2O3 |
| Regeneration @ 400 C. | YES | YES | YES |
| Feedstock | PA | MP | HOAc |
| Temperature, ° C. | 350 | 350 | 350 |
| GHSV, hr-1 | 500 | 520 | 500 |
| Mol. Frac. DME | 0.2068 | 0.1992 | 0.2064 |
| Mol. Frac. PA | 0.2495 | 0.2771 | 0.251 |
| Mol. Frac. O2* | 0.0544 | 0.0524 | 0.0543 |
| DME/Feedstock Ratio | 0.82 | 0.72 | 0.82 |
| DME/O2 Ratio | 3.8 | 3.8 | 3.8 |
| | Conversion | Conversion | Conversion |
| % DME | 60 | 31 | 71 |
| % PA | 92 | 36 | 81 |
| | Selectivity | Selectivity | Selectivity |
| % C, DME-based | | | |
| CO | 6.4 | 14.0 | 8.6 |
| CH4 | 0.0 | 0.0 | 0.0 |
| CO2 | 9.5 | 17.5 | 6.6 |
| MeOH | 5.4 | 6.0 | 4.3 |
| methyl formate | 0.0 | 0.0 | 0.0 |
| % C, PA-based | | | |
| methyl propionate | 88.1 | N/A | 0.3 |
| methyl isobutyrate | 0.5 | 3.3 | 0.0 |
| acetone | 0.1 | 0.4 | 0.2 |
| methyl methacrylate | 1.3 | 5.9 | 0.0 |
| propanal | 0.1 | 0.4 | 0.0 |
| isobutyric acid | 0.1 | 0.0 | 0.0 |
| propionic acid | N/A | 41.4 | 0.0 |
| methacrylic acid | 0.0 | 0.0 | 0.0 |
| acrylic acid | 0.0 | 0.0 | 0.0 |
| acetaldehyde | 6.6 | 28.7 | 0.5 |
| methyl acetate | 1.2 | 10.1 | 99.0 |
| ethyl propionate | 0.1 | 0.6 | 0.0 |
| diethylketone | 2.0 | 9.0 | 0.0 |
| methyl acrylate | 0.0 | 0.0 | 0.4 |
| Total Carbon Balance | 74.0 | 74.0 | 105.3 |

*Balance is $N_2$, i.e., Mole Fraction (DME + PA + $O_2$ + $N_2$) = 1.0

TABLE 5

| Example No. | 13 | 14 | 15 | 16 | 17 |
|---|---|---|---|---|---|
| Catalyst | HZSM5 | HZSM5 | HZSM5 | LA 30 | LA 30 |
| Temperature, ° C. | 275 | 330 | 350 | 300 | 330 |
| GHSV, hr-1 | 920 | 920 | 920 | 920 | 920 |
| Mol. Ftac. DME | 0.2061 | 0.2061 | 0.2061 | 0.2063 | 0.2062 |
| Mol. Frac. PA | 0.2515 | 0.2515 | 0.2515 | 0.2513 | 0.2513 |
| Mol. Frac. O2* | 0.0543 | 0.0543 | 0.0543 | 0.0542 | 0.0542 |
| | Conversion | Conversion | Conversion | Conversion | Conversion |
| % DME | 92 | 78 | 66 | 32 | 38 |
| % PA | 90 | 45 | 72 | 33 | 23 |
| | Selectivity | Selectivity | Selectivity | Selectivity | Selectivity |
| % C, DME-based | | | | | |
| CO | 5.7 | 10.1 | 10.0 | 7.0 | 4.2 |

TABLE 5-continued

| Example No. | 13 | 14 | 15 | 16 | 17 |
|---|---|---|---|---|---|
| CH4 | 1.0 | 1.0 | 1.0 | 0.1 | 0.3 |
| CO2 | 3.0 | 10.4 | 16.8 | 13.3 | 15.7 |
| MeOH | 2.7 | 1.6 | 5.1 | 0.0 | 0.2 |
| methyl formate | 0.0 | 0.0 | 0.0 | 0.0 | 0.0 |
| % C, PA-based | | | | | |
| methyl propionate | 96.4 | 90.2 | 91.4 | 68.9 | 70.5 |
| methyl isobutyrate | 0.5 | 0.4 | 0.0 | 0.0 | 0.0 |
| acetone | 0.0 | 0.0 | 0.0 | 0.0 | 0.0 |
| methyl methacrylate | 0.0 | 0.3 | 0.3 | 0.0 | 0.2 |
| propanal | 0.0 | 0.0 | 0.0 | 0.0 | 0.0 |
| isobutyric acid | 0.0 | 0.1 | 0.0 | 1.3 | 0.7 |
| butyric acid | 0.0 | 0.0 | 0.0 | 0.0 | 0.0 |
| methacrylic acid | 0.0 | 0.0 | 0.0 | 1.1 | 6.2 |
| acrylic acid | 0.0 | 0.0 | 0.0 | 0.0 | 0.0 |
| acetaldehyde | 1.7 | 4.6 | 4.7 | 24.9 | 17.0 |
| methylacetate | 1.5 | 2.3 | 1.9 | 1.9 | 1.1 |
| ethyl propionate | 0.0 | 0.0 | 0.0 | 0.0 | 0.0 |
| diethylketone | 0.0 | 2.6 | 1.7 | 1.9 | 4.5 |
| acetic acid | 0.0 | 0.0 | 0.0 | 0.0 | 0.0 |
| Total Carbon Balance | 100.9 | 92.9 | 96.3 | 81.7 | 96.5 |

*Balance is $N_2$, i.e., Mole Fraction (DME + PA + $O_2$ + $N_2$) = 1.0

TABLE 6

| Example No. | 18 | 19 | 21 | 22 |
|---|---|---|---|---|
| Catalyst | Mo/Al2O3 | Mo/Al2O3 | K/Mo/Al2O3 | K/Mo/Al2O3 |
| Temperature, ° C. | 300 | 350 | 300 | 330 |
| GHSV, hr-1 | 920 | 920 | 920 | 920 |
| Mol. Frac. DME | 0.2062 | 0.2062 | 0.2063 | 0.2061 |
| Mol. Frac. PA | 0.2513 | 0.2513 | 0.2513 | 0.2515 |
| Mol. Frac. O2* | 0.0543 | 0.0543 | 0.0542 | 0.0543 |
| | Conversion | Conversion | Conversion | Conversion |
| % DME | 38 | 69 | 14 | 12 |
| % PA | 30 | 73 | 23 | 17 |
| | Selectivity | Selectivity | Selectivity | Selectivity |
| % C, DME-based | | | | |
| CO | 2.8 | 9.5 | 11.2 | 13.6 |
| CH4 | 0.0 | 0.4 | 0.0 | 0.0 |
| CO2 | 6.8 | 10.3 | 69.2 | 60.5 |
| MeOH | 0.0 | 2.8 | 0.0 | 0.0 |
| methyl formate | 0.0 | 0.0 | 0.0 | 0.0 |
| % C, PA-based | | | | |
| methyl propionate | 30.0 | 84.2 | 0.0 | 5.4 |
| methyl isobutyrate | 0.0 | 0.7 | 0.0 | 0.0 |
| acetone | 0.0 | 0.0 | 0.0 | 0.0 |
| methyl methacrylate | 0.0 | 1.1 | 0.0 | 0.0 |
| propanal | 0.0 | 0.1 | 0.0 | 0.0 |
| isobutyric acid | 2.0 | 0.2 | 2.3 | 4.0 |
| butyric acid | 0.0 | 0.0 | 0.0 | 0.0 |
| methacrylic acid | 0.5 | 0.7 | 0.0 | 0.0 |
| acrylic acid | 3.0 | 0.3 | 0.0 | 0.0 |
| acetaldehyde | 40.1 | 4.6 | 81.8 | 36.9 |
| methylacetate | 0.0 | 2.3 | 0.0 | 0.0 |
| ethyl propionate | 3.2 | 0.2 | 0.0 | 0.0 |
| diethylketone | 8.5 | 2.7 | 15.9 | 53.6 |
| acetic acid | 12.7 | 1.3 | 0.0 | 0.0 |
| Total Carbon Balance | 74.6 | 79.8 | 88.2 | 79.9 |

*Balance is $N_2$, i.e., Mole Fraction (DME + PA + $O_2$ + $N_2$) = 1.0

TABLE 7

| Example No. | 24 | 26 | 28 | 29 |
|---|---|---|---|---|
| Catalyst | Ti/Al2O3 | Mo/Ti/Al2O3 | Bi6Mo2O15 | Bi6Mo2O15 |
| Temperature, °C. | 350 | 300 | 300 | 350 |
| GHSV, hr-1 | 920 | 920 | 920 | 920 |
| Mol. Frac. DME | 0.2061 | 0.2061 | 0.2062 | 0.2062 |
| Mol. Frac. PA | 0.2515 | 0.2515 | 0.2513 | 0.2513 |
| Mol. Frac. O2* | 0.0543 | 0.0543 | 0.0543 | 0.0543 |
| | Conversion | Conversion | Conversion | Conversion |
| % DME | 42 | 42 | 40 | 41 |
| % PA | 12 | 39 | 37 | 39 |
| | Selectivity | Selectivity | Selectivity | Selectivity |
| % C, DME-based | | | | |
| CO | 3.6 | 7.0 | 2.8 | 5.4 |
| CH4 | 0.0 | 0.2 | 0.0 | 0.0 |
| CO2 | 9.7 | 18.5 | 22.5 | 30.6 |
| MeOH | 0.0 | 0.3 | 0.0 | 0.0 |
| methyl formate | 0.0 | 0.0 | 0.0 | 0.0 |
| % C, PA-based | | | | |
| methyl propionate | 36.6 | 53.9 | 0.5 | 2.5 |
| methyl isobutyrate | 0.0 | 0.2 | 0.0 | 0.0 |
| acetone | 0.0 | 0.1 | 0.0 | 0.0 |
| methyl methacrylate | 0.0 | 0.0 | 0.0 | 0.0 |
| propanal | 0.0 | 0.1 | 0.0 | 0.0 |
| isobutyric acid | 1.7 | 0.4 | 2.0 | 1.8 |
| butyric acid | 0.0 | 0.0 | 0.0 | 0.0 |
| methacrylic acid | 0.5 | 1.0 | 0.0 | 0.0 |
| acrylic acid | 0.0 | 3.1 | 0.0 | 0.0 |
| acetaldehyde | 33.2 | 24.6 | 62.3 | 88.1 |
| methyl acetate | 0.0 | 2.4 | 0.0 | 0.0 |
| ethyl propionate | 1.0 | 1.1 | 0.0 | 0.0 |
| diethylketone | 18.3 | 0.8 | 35.2 | 7.7 |
| acetic acid | 7.6 | 12.4 | 0.0 | 0.0 |
| Total Carbon Balance | 87.5 | 83.4 | 69.1 | 67.9 |

*Balance is $N_2$, i.e., Mole Fraction (DME + PA + $O_2$ + $N_2$) = 1.0

TABLE 8

| Example No. | 30 | 31 | 33 | 34 | 36 |
|---|---|---|---|---|---|
| Catalyst | FePO4 | FePO4 | 1% V2O5/SiO2 | 1% V2O5/SiO2 | V-Si-P |
| Temperature, °C. | 300 | 330 | 300 | 330 | 350 |
| GHSV, hr-1 | 920 | 920 | 920 | 920 | 920 |
| Mol. Frac. DME | 0.2063 | 0.2063 | 0.2063 | 0.2063 | 0.2061 |
| Mol. Frac. PA | 0.2513 | 0.2513 | 0.2513 | 0.2513 | 0.2515 |
| Mol. Frac. O2* | 0.0542 | 0.0542 | 0.0542 | 0.0542 | 0.0543 |
| | Conversion | Conversion | Conversion | Conversion | Conversion |
| % DME | 34 | 36 | 23 | 24 | 59 |
| % PA | 35 | 17 | 30 | 20 | 65 |
| | Selectivity | Selectivity | Selectivity | Selectivity | Selectivity |
| % C, DME-based | | | | | |
| CO | 3.5 | 11.5 | 5.1 | 3.0 | 7.6 |
| CH4 | 0.1 | 0.1 | 0.1 | 0.2 | 0.0 |
| CO2 | 24.4 | 11.9 | 27.4 | 38.0 | 6.9 |
| MeOH | 0.0 | 0.0 | 0.0 | 0.0 | 0.7 |
| methyl formate | 0.0 | 0.9 | 0.0 | 0.0 | 0.0 |
| % C, PA-based | | | | | |
| methyl propionate | 11.6 | 22.2 | 2.7 | 2.4 | 89.9 |
| methyl isobutyrate | 0.0 | 0.0 | 0.0 | 0.0 | 0.0 |
| acetone | 0.1 | 0.0 | 0.0 | 0.0 | 0.0 |
| methyl methacrylate | 0.0 | 0.0 | 0.0 | 0.0 | 0.0 |
| propanal | 0.0 | 0.0 | 0.0 | 0.0 | 0.0 |
| isobutyric acid | 0.7 | 1.3 | 1.4 | 1.4 | 0.1 |
| butyric acid | 0.0 | 0.0 | 0.0 | 0.0 | 0.0 |
| methacrylic acid | 0.3 | 0.0 | 0.0 | 0.0 | 0.0 |
| acrylic acid | 2.7 | 8.4 | 0.0 | 1.3 | 0.1 |
| acetaldehyde | 66.3 | 53.5 | 75.0 | 76.2 | 7.9 |
| methyl acetate | 0.0 | 0.0 | 0.0 | 0.0 | 0.7 |
| ethyl propionate | 1.3 | 0.0 | 6.0 | 4.6 | 0.6 |

TABLE 8-continued

| Example No. | 30 | 31 | 33 | 34 | 36 |
|---|---|---|---|---|---|
| diethylketone | 0.0 | 0.0 | 8.3 | 9.1 | 0.0 |
| acetic acid | 16.9 | 14.6 | 6.6 | 5.0 | 0.6 |
| Total Carbon Balance | 77.3 | 86.2 | 82.4 | 89.0 | 72.1 |

*Balance is $N_2$, i.e., Mole Fraction (DME + PA + $O_2$ + $N_2$) = 1.0

TABLE 9

| RUN No. | 37A | 37B | 37C | 38A | 38B |
|---|---|---|---|---|---|
| Catalyst | g-Al2O3 | g-Al2O3 | g-Al2O3 | g-Al2O3 | g-Al2O3 |
| Heated @ 400 C. in 10% O2 | yes | yes | yes | yes | yes |
| Temperature, °C. | 350 | 350 | 350 | 350 | 350 |
| GHSV, hr-1 | 500 | 725 | 920 | 920 | 500 |
| Mol. Frac. DME | 0.4223 | 0.4175 | 0.4165 | 0.4220 | 0.4221 |
| Mol. Frac. MP | 0.1048 | 0.1041 | 0.1060 | 0.1060 | 0.1061 |
| Mol. Frac. O2* | 0.0556 | 0.0555 | 0.0555 | 0.0205 | 0.0204 |
| DME/MP Ratio | 4.03 | 4.07 | 3.98 | 3.98 | 3.98 |
| DME/O2 Ratio | 7.60 | 7.63 | 7.61 | 20.6 | 20.7 |
|  | Conversion | Conversion | Conversion | Conversion | Conversion |
| % DME | 34.3 | 56.9 | 55.1 | 40.7 | 32.1 |
| % MP | 24.1 | 25.3 | 24.2 | 30.7 | 11.2 |
|  | Selectivity | Selectivity | Selectivity | Selectivity | Selectivity |
| % C, DME-based |  |  |  |  |  |
| CO | 6.8 | 4.8 | 5.2 | 3.9 | 3.0 |
| CH4 | 0.0 | 0.0 | 0.0 | 0.0 | 0.0 |
| CO2 | 8.8 | 4.5 | 4.6 | 3.3 | 4.1 |
| MeOH | 5.2 | 3.0 | 3.0 | 2.9 | 3.3 |
| methyl formate | 0.0 | 0.0 | 0.0 | 0.0 | 0.0 |
| % C, PA-based |  |  |  |  |  |
| methyl propionate | N/A | N/A | N/A | N/A | N/A |
| methyl isobutyrate | 5.3 | 3.6 | 3.2 | 6.5 | 6.7 |
| acetone | 2.3 | 2.0 | 1.7 | 1.7 | 1.2 |
| methyl methacrylate | 14.4 | 12.7 | 14.8 | 22.7 | 17.8 |
| propanal | 0.6 | 0.6 | 0.5 | 0.5 | 0.5 |
| isobutyric acid | 1.2 | 0.6 | 1.1 | 1.7 | 0.5 |
| propionic | 37.2 | 48.9 | 51.4 | 42.6 | 31.8 |
| methacryic acid | 2.0 | 1.3 | 1.7 | 2.8 | 2.3 |
| acrylic acid | 5.9 | 2.4 | 2.8 | 4.5 | 3.7 |
| acetaldehyde | 13.7 | 13.9 | 9.9 | 0.0 | 15.8 |
| methyl acetate | 10.9 | 8.4 | 8.4 | 7.5 | 9.0 |
| ethyl propionate | 0.0 | 0.0 | 0.0 | 0.0 | 0.0 |
| diethylketone | 3.3 | 2.3 | 1.4 | 3.9 | 5.7 |
| methyl acrylate | 0.1 | 0.2 | 0.2 | 0.0 | 0.0 |
| Total Carbon Balance | 78.3 | 62.4 | 63.4 | 67.9 | 80.2 |

*Balance N2

TABLE 10

|  | Ex. 37A | Ex. 37B | Ex. 37C |
|---|---|---|---|
| GHSV | 500 | 725 | 920 |
| "Single-Pass" Conversion (%) | 14.8 | 12.5 | 11.4 |
| % MMA + MAA | 27.5 | 29.2 | 36.1 |
| % MIB + IBA | 10.9 | 8.8 | 9.4 |
| % ACH | 22.9 | 29.0 | 21.7 |
| % DEK | 5.5 | 4.8 | 3.1 |
| % Other | 33.2 | 28.3 | 29.8 |
| DME/$O_2$ | 7.6 | 7.6 | 7.6 |

TABLE 11

|  | Ex. 38A | Ex. 38B |
|---|---|---|
| GHSV | 920 | 500 |
| "Single-Pass" Conversion (%) | 16.8 | 7.5 |
| % MMA + MAA | 49.2 | 31.8 |
| % MIB + IBA | 15.8 | 11.4 |
| % ACH | 0.0 | 25.0 |
| % DEK | 7.5 | 9.0 |
| % Other | 27.4 | 22.8 |
| DME/$O_2$ | 20.6 | 20.7 |

What is claimed is:

1. A process for methylating an alpha carbon adjacent to an electron withdrawing group, said process comprising:

providing a molecule containing said alpha carbon and said electron withdrawing group; and reacting said molecule in a presence of an acid catalyst with dimethyl ether to substitute a methyl group on said alpha carbon.

2. The process of claim 1, wherein said molecule and said dimethyl ether are combined in a vapor phase.

3. The process of claim 2, wherein said molecule is provided in a feedstock comprising propionic acid and methyl propionate.

4. The process of claim 3, wherein said molecule is at least one member selected from the group consisting of propionic acid and methyl propionate.

5. The process of claim 2, wherein said reacting is represented by Equation I:

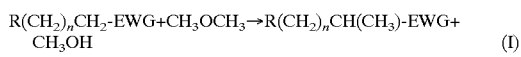

$$R(CH_2)_nCH_2\text{-}EWG + CH_3OCH_3 \rightarrow R(CH_2)_nCH(CH_3)\text{-}EWG + CH_3OH \quad (I)$$

where EWG is said electron withdrawing group, and R is H when n is 0, 1 or 2, and R is alkyl, EWG or aryl when n>2.

6. The process of claim 5, wherein said molecule is a member selected from the group consisting of acetic acid, propionic acid, methyl acetate, methyl propionate, acetonitrile, propionitrile and acetone.

7. The process of claim 5, wherein said electron withdrawing group is a member selected from the group consisting of carboxylic acids, carboxylic acid esters, nitriles, aromatic rings and ketones.

8. The process of claim 5, wherein said acid catalyst comprises a Lewis acid functionality.

9. The process of claim 5, wherein said acid catalyst is a member selected from the group consisting of gamma-alumina, amorphous silica-alumina, a steam-treated zeolite, an acid washed clay, an alumina impregnated clay, and $MoO_3$ on gamma-alumina.

10. The process of claim 9, wherein said steam-treated zeolite is ultra-stable Y.

11. The process of claim 5, wherein said process is conducted without a basic catalyst.

12. The process of claim 5, wherein a DME/M ratio of dimethyl ether to said molecule ranges from about 0.5 to about 20.

13. The process of claim 5, wherein said reacting is conducted at a temperature from about 150° C. to about 500° C.

14. The process of claim 13, wherein said temperature is from 250° C. to 400° C.

15. The process of claim 5, wherein said reacting is conducted at a pressure from 0 to 50 psig.

16. The process of claim 5, wherein a total feed space velocity is from about 100 to about 5000 $hr^{-1}$.

17. The process of claim 16, wherein said total feed space velocity is from 200 to 2000 $hr^{-1}$.

18. The process of claim 2, wherein said electron withdrawing group is an acid, and said process further comprises forming a methyl ester by esterifying said electron withdrawing group with methanol liberated from said dimethyl ether.

19. The process of claim 2, further comprising dehydrogenating said methyl group in a presence of an oxidant to produce an $\alpha,\beta$-unsaturated bond in said molecule.

20. The process of claim 19 wherein said oxidant is a member selected from the group consisting of oxygen, air and oxygen-enriched air.

21. The process of claim 20 wherein said oxidant is oxygen gas.

22. The process of claim 21, wherein said process is represented by Equation II:

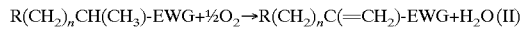

$$R(CH_2)_nCH(CH_3)\text{-}EWG + \tfrac{1}{2}O_2 \rightarrow R(CH_2)_nC(=CH_2)\text{-}EWG + H_2O \quad (II)$$

where EWG is said electron withdrawing group, and R is H when n is 0, 1 or 2, and R is alkyl, EWG or aryl when n>2.

23. The process of claim 22, wherein said molecule is propionic acid and a product of said reacting is methyl methacrylate.

24. The process of claim 19, wherein a $DME/O_2$ ratio of dimethyl ether to oxygen ranges from about 1 to about 25.

* * * * *